United States Patent [19]
Stern

[11] Patent Number: 6,063,051
[45] Date of Patent: May 16, 2000

[54] PHOTOMETRY SYSTEM FOR ANALYZING FLUIDS

[75] Inventor: Roger A. Stern, Cupertino, Calif.

[73] Assignee: Aquintel, Inc., Mountain View, Calif.

[21] Appl. No.: 09/102,926

[22] Filed: Jun. 22, 1998

Related U.S. Application Data

[63] Continuation-in-part of application No. 08/965,549, Nov. 6, 1997.

[51] Int. Cl.$^7$ ...................................................... A61B 5/00
[52] U.S. Cl. ............................ 604/27; 604/318; 600/579; 600/584
[58] Field of Search .................................. 600/309, 310, 600/322, 573, 578, 579, 584; 604/27–30, 65–67, 317, 318, 322

[56] References Cited

U.S. PATENT DOCUMENTS

| | | | |
|---|---|---|---|
| 4,195,641 | 4/1980 | Joines et al. | |
| 4,464,172 | 8/1984 | Lichtenstein | 604/65 |
| 5,085,499 | 2/1992 | Griffin et al. | 356/311 |
| 5,278,629 | 1/1994 | Schlager et al. | 356/313 |
| 5,285,251 | 2/1994 | Pilloud et al. | 356/313 |
| 5,331,958 | 7/1994 | Oppenheimer | 600/322 |

OTHER PUBLICATIONS

J. C. Mills and R. J. Hodges, Fiber Optics Expand the Range of a Direct–Reading Spark Optical Emission Spectrometer, Applied Spectroscopy, vol. 38, No. 3, 1984, pp. 413–416.

David A. Cremers et al., Spectrochemical Analysis of Liquids Using the Laser Spark, Applied Spectroscopy, vol. 38, No. 5, 1984, pp. 721–729.

*Primary Examiner*—Eric F. Winakur
*Attorney, Agent, or Firm*—Carr & Ferrell LLP

[57] ABSTRACT

A computer based system for tracking a patient's fluid volume and electrolyte (cation or anion concentration) balances, during the period extending from before surgical procedures through the recovery process, which will assist the attending physician in maintaining proper balances in the patient. The system contains automatic sensors for measuring the volumes of fluids administered to and recovered from the patient. The system also preferably contains sensors for measuring electrolyte concentrations in these fluids, and, when sensors are not available, assists the attending physician in estimating. The system assists the attending physician in creating baseline values for a patient's fluid and electrolyte values, and then accounts for the fluids going into and out of the patient to continuously track current values. Out of bounds conditions for these balances, when detected, will cause the system to issue alarms and make suggestions to the attending physician for remedial action.

8 Claims, 11 Drawing Sheets

Fig. 4 Composition of IV Fluids

| Type of IV Fluid | Sodium mmol/L | Potassium mmol/L | Chloride mmol/L | Bicarbonate mmol/L | Glucose mmol/L | Common Name |
|---|---|---|---|---|---|---|
| Normal saline | 154 | 0 | 154 | 0 | 0 | NS |
| Half-normal saline | 77 | 0 | 77 | 0 | 0 | 1/2 NS |
| 5% dextrose in water | 0 | 0 | 0 | 0 | 280 | D5/W |
| 3% hypertonic saline | 514 | 0 | 514 | 0 | 0 | hypertonic Saline |
| Ringers lactate | 130 | 4 | 112 | 28 | 0 | RL |
| 5% dextrose in saline | 154 | 0 | 154 | 0 | 280 | D5/NS |
| 5% dextrose in Ringers lactate | 130 | 4 | 112 | 28 | 280 | D5/RL |
| 5% sodium bicarbonate | 595 | 0 | 0 | 595 | 0 | |
| Blood plasma | 140 | 4 | 105 | 26 | 6 | |
| Whole blood | 140 | 4 | 105 | 26 | 6 | |
| Blood fractions (platelets, clotting factors, fibrinogen) | 0 | 0 | 0 | 0 | 0 | |

Fig. 5 ELECTROLYTE CONTENT OF BODY FLUIDS

Mean concentration (mmol/liter) followed by normal ranges of four predominant electrolytes

| Fluid | | Na+ | K+ | Cl- | HC03- |
|---|---|---|---|---|---|
| Plasma | Mean value | 140 | 4.5 | 102 | 26 |
| | Range | 137-142 | 3.5-5.0 | 99-104 | 23-28 |
| Saliva | Mean value | 33 | 20 | 34 | |
| | Range | 20-46 | 16-23 | 24-44 | |
| Gastric juice | Mean value | 60 | 9 | 84 | 0 |
| | Range | 30-90 | 4.3-12 | 52-124 | |
| Bile | Mean value | 149 | 4.9 | 101 | 45 |
| | Range | 120-170 | 3-12 | 80-120 | 30-50 |
| Pancreatic juice | Mean value | 141 | 4.6 | 77 | 92 |
| | Range | 113-153 | 2.6-7.4 | 54-95 | 70-110 |
| Small bowel | Mean value | 105 | 5.1 | 99 | 50 |
| | Range | 72-158 | 3.5-6.8 | 70-127 | 20-40 |
| Ileal fluid | Mean value | 129 | 11.2 | 116 | 29 |
| | Range | 90-140 | 6-30 | 82-125 | 25-30 |
| Cecal fluid | Mean value | 80 | 21 | 48 | 22 |
| | Range | 50-116 | 11-28 | 35-70 | 15-30 |
| Cerebrospinal fluid | Mean value | 141 | 2.9 | 127 | 23 |
| | Range | 135-147 | 2.5-3.4 | 116-132 | 21-25 |
| Perspiration | Mean value | 45 | 4.5 | 58 | 0 |
| | Range | 18-97 | 2.0-10 | 18-97 | |

AQUINTEL™ I/OMeter

| PATIENT | 123456 | | | | | | |
|---|---|---|---|---|---|---|---|
| SEX | AGE | HEIGHT | WEIGHT | BMI | | TBW | TBC |
| F | 30 | 5'2" | 127 lbs | 23.3 | | 28 L | 3864 mmol |

FLUIDS ADMINISTERED

| FLUID | VOLUME | CATION CONCENTRATION | CUMULATIVE TBW | TOTAL CATION CHANGE |
|---|---|---|---|---|
| ▲ RINGERS | +4000mL | +133 mmol/L | +32000 mL | +532 mmol |
| DEXTROSE | +2000mL | + 0 mmol/L | +34000 mL | + 0 mmol |
| CHANGE | +6000 mL | | | +532 mmol |

FLUIDS COLLECTED

| FLUID | VOLUME | CATION CONCENTRATION | CUMULATIVE TBW | TOTAL CATION CHANGE |
|---|---|---|---|---|
| ▲ URINE | -3100 mL | -75 mmol | +30900 mL | -233 mmol |
| ▲ GASTRIC | -3600mL | -120 mmol | +27300 mL | -432 mmol |
| CHEST | | | | |
| BILIARY | | | | |
| BLOOD | -1800 mL | -140 mmol | +25500 mL | -252 mmol |
| EMESIS | | | | |
| DIARRHEA | | | | |
| CHANGE | -8500 mL | | | -917 mmol |

NET FLUID AND ELECTROLYTE BALANCE

| | VOLUME | CATION CONCENTRATION | CUMULATIVE TBW | TOTAL CATION CHANGE |
|---|---|---|---|---|
| | -2500 mL | 136 mmol/L | +25500mL | -385 mmol |

| | total body water, liters, running total | gains | losses | source | total body cation, mmoles, running total | gains | losses | source | cation concentration mmol/L |
|---|---|---|---|---|---|---|---|---|---|
| pre-op | 28 liters | | | | 3864 | | | | |
| during surgery | 32 | 4 | | Ringers lactate | 4396 | 532 | | Ringers lactate | 133 |
| during surgery | 30.2 | | 1.8 | blood loss | 4144 | | 252 | blood loss | 140 |
| after surgery | 30.2 | | | | 4144 | | | | |
|  | 26.6 | | 3.6 | gastric suction | 3712 | | 432 | gastric suction | 120 |
|  | 23.5 | | 3.1 | urine | 3480 | | 232 | urine | 75 |
|  | 25.5 | 2 | | IV 5% dextrose | 3480 | 0 | | | 0 |
| net water deficit | 2.5 liters | | | | | | | | |
| net cation deficit | | | | | 384 mmoles | | | | |
| post op balance | 25.5 | | | | 3480 mmoles | | | | |

Fig. 12

PHOTOMETRY SYSTEM FOR ANALYZING FLUIDS

CROSS-REFERENCE TO RELATED APPLICATION

This application is a continuation-in-part of application serial number 08/965,549 which was filed on Nov. 6, 1997, and which is hereby incorporated by reference.

BACKGROUND OF THE INVENTION

1. Field of the Invention

The present invention relates generally to patient fluid monitoring systems and more specifically to monitoring systems using flame photometry.

2. Discussion of the Prior Art

Human patients undergoing surgery lose fluids which require replacement at rates depending upon the location and type of surgery. Peripheral procedures require the least fluids while intra-abdominal procedures require the most. Some procedures even introduce more fluid into patients than is removed. Procedures such as transurethral bladder and prostate resections, and hysteroscopic vaginal hysterectomies using large volumes of irrigating solutions may result in absorption of significant amounts of the irrigating solution accompanied by increased intravascular volume and the dangers of congestive heart failure and hyponatremia (see J. C. Ayus & A. I. Arieff, Glycine-induced Hypoosmolar Hyponatremia, 157 Arch. Intern. Med. 223 (1997), which is hereby incorporated by reference).

Much of the rationale for administering large quantities of postoperative fluids, despite the attendant dangers of pulmonary edema, includes the effects of the "third space," regions in the body occupied by fluids which are not in equilibrium with the bloodstream. Examples of the third space include burns, bruises, traumatized operative bed (intra-abdominal or intra-thoracic), traumatically injured tissues, and infarcted tissues. Fluids in the third space are literally out of circulation and therefore hemodynamically inactive. Fluid sequestration in the third space is a circulation and therefore hemodynamically inactive. Fluid sequestration in the third space is a unique kind of fluid loss in postoperative patients (see M. H. Rosenthal & A. I. Arieff, Fluid and Electrolyte Therapy in Critically Ill Patients and Those Who Are Pre-, Post-, or Intraoperative, in Fluid, Electrolyte and Acid-Base Disorders 597 (A. I. Arieff & R. A. DeFronzo eds., 1995), which is hereby incorporated by reference).

However, there is no simple bedside method for accurately measuring these fluid losses, and in actual practice clinical approximation determines replacement. The sequestered extracellular fluid (third space losses) postoperatively during an uncomplicated procedure varies between negligible and 3 liters. Quantification of functional extracellular fluid using the available means of measuring is extremely difficult, and consequently no accurate a priori formula for intraoperative fluid administration has been derived.

Postoperative fluid balance depends on underlying pathology factors including anesthesia, intraoperative fluid therapy and intra- and post-operative complications. Humoral mediators (such as the renin-angiotensin system, catecholamines, aldosterone, and AVP), which can influence hemodynamics and are released during surgery as described below, may persist into the postoperative period and require continuous administration of large volumes of fluids. While the intravascular volume must be maintained to avoid postoperative renal insufficiency, too much postoperative fluid can result in heart and lung failure with pulmonary edema. The potential postoperative complication of pulmonary edema and respiratory failure is a major hazard which discourages administering fluids in sufficient quantities to maintain preload.

The quantity of fluid necessary to induce pulmonary edema varies according to individual patient factors such as age, body weight, tissue turgor, cardiac function, pulmonary function, renal function, plasma vasopressin levels, and plasma proteins. The literature includes some information concerning minimal quantities of fluid which could induce pulmonary edema in otherwise generally healthy postoperative patients, but this information does not imply that any given quantity of fluid will necessarily induce pulmonary edema. Little information is available concerning the maximum postoperative volume of fluid which can be safely administered. In particular, it is not clear what volume of fluid might result in pulmonary edema in a postoperative patient who does not have serious cardiovascular, hepatic or renal disorders.

Figure 1:
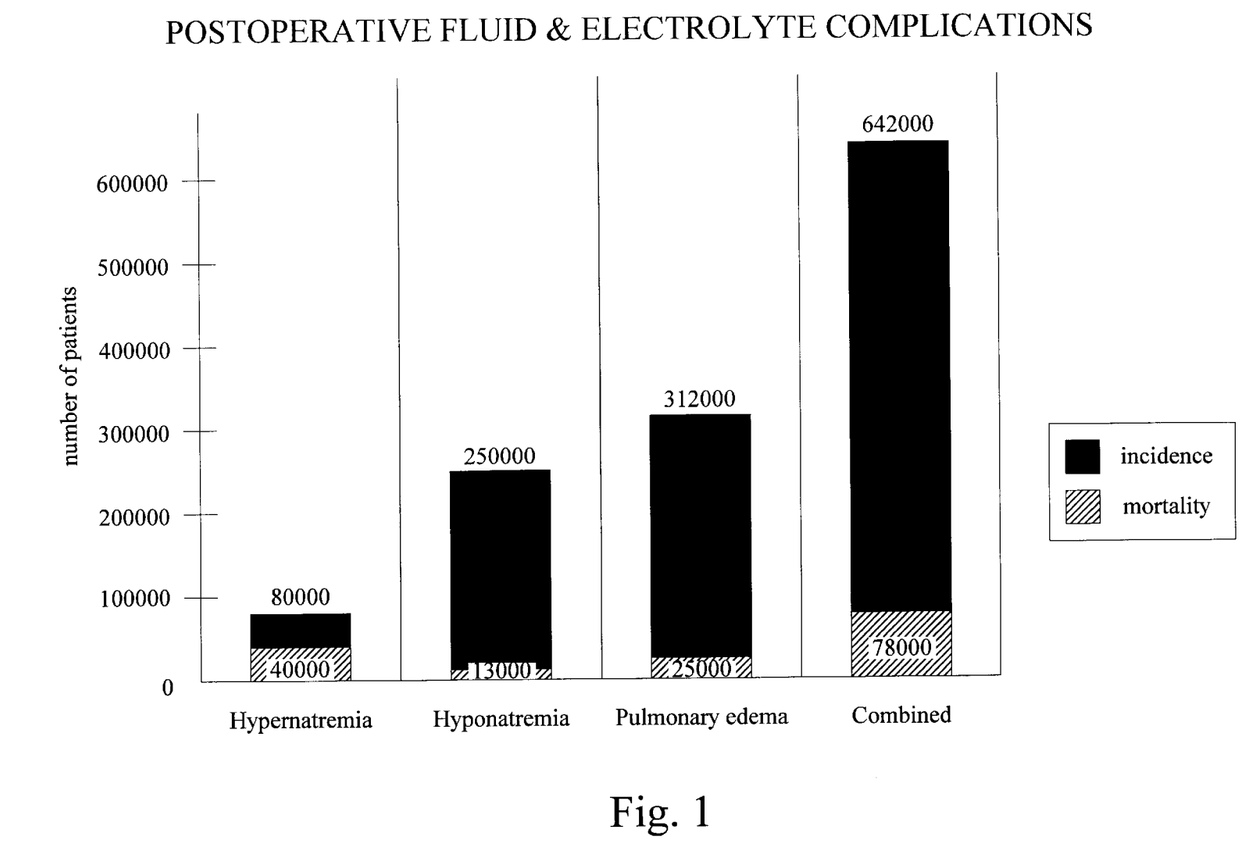
FIG. 1 is a bar chart summarizing postoperative complications.

As shown in FIG. 1, three major postoperative complications, hypernatremia, hyponatremia, and pulmonary edema affect almost 650,000 postoperative patients, with an estimated mortality of 78,000 individuals, per year in the USA (see M. H. Rosenthal & A. I. Arieff, Fluid and Electrolyte Therapy in Critically Ill Patients and Those Who Are Pre-, Post-, or Intraoperative, in Fluid, Electrolyte and Acid-Base Disorders 597–632 (A. I. Arieff & R. A. DeFronzo eds., Churchill Livingstone, N.Y., 1995).

The art related to the field of systematic monitoring of the fluid and electrolyte balances in patients includes partial solutions to the above-described problems. There is no prior art comprehending a systematic approach which can warn physicians when a major problem (hyponatremia, hypernatremia, pulmonary edema) is imminent, and give meaningful suggestions to an attending physician. In many hospitals' operating rooms the fluid input and output volumes are roughly estimated by an attending physician aided only by his or her visual observations and experience.

Among prior inventions directed towards certain aspects of the fluid and electrolyte balance problem, Parrish (U.S. Pat. No. 4,448,207) and Blankenship, et al. (U.S. Pat. No. 4,658,834) both disclose apparatuses using sonic transducers for measuring of the volume of fluids outgoing from a patient. Corbitt, et al. (U.S. Pat. No. 4,449,538) discloses an apparatus which measures bulk fluid input and output volumes and advises an attending physician, but not on electrolyte balance. Cormier, et al. (U.S. Pat. No. 4,531,088) discloses in-line blood analysis through electrical resistance measuring, and Oppenheimer (U.S. Pat. No. 5,331,958) does the same through laser beams. Micklish (U.S. Pat. No. 5,285,682) addresses the problem of measuring the volume of fluid absorbed in sponges. Ludwigsen (U.S. Pat. No. 5,236,664) addresses the problem of losing blood in non-fluid forms by measuring levels of hemoglobin in blood-containing materials to estimate total blood loss.

Measurement of the concentration of electrolytes, in particular sodium and potassium, in body fluids such as blood or urine has been aimed almost exclusively at getting high accuracy readings about some nominal normal body level. There are several ways of doing this, for example using a device called a flame photometer in which the thermal energy of a flame ionizes some atoms from a sample, emissions from which color the flame to obtain a quantitative estimate of the properties of the fluid being analyzed. The most often used emission lines for sodium and potassium are sodium at 589 nm and potassium 767 nm. The prior art also describes the use of sparks, including sparks created by lasers and by either DC or AC electrical discharges. The prior art generates a spark by using two electrodes immersed in the fluid. This poses problems associated with unknown effects that the optical properties of the fluid might have. For example, if two fluids contained the same electrolyte concentrations but one was a different color than the other, the resulting light emitted and available for analysis might be affected. In addition, the fluid composition is highly variable, may be full of debris, and is potentially infectious.

For purposes of patient fluid monitoring it is important to know or measure electrolyte concentrations in input and output fluids, which can vary significantly, although accuracy within twenty percent is probably good enough. It is also desirable that the sensor be disposable and inexpensive.

SUMMARY OF THE INVENTION

Towards solving the problems discussed above, this invention has as an object to present advisory information about a patient's fluid and electrolyte balances, on an at least near-real-time basis, to an attending physician.

The invention provides a digital computer-based system for measuring the fluid volume and, to the extent possible, ionic composition. When direct measurements are not feasible the invention will assist a physician in estimating the ionic composition. Sensors for measuring fluid volume flow and fluid cation or anion levels may be connected to the ingoing and outgoing fluid streams. Alternatively, fluids may be sampled and analyzed in order to determine ionic composition. The invention preferably can also print a history of a patient's fluid and electrolyte status.

Fluids entering a patient usually have standard parameters for cation or anion concentration, and accurate, quantitative sensors may be replaced by either more cost-effective confirmation sensors (confirming whether the Operating Room technician hung the right bag), by an operator entry, or by bar code.

The exiting fluids (emesis, blood, urine, etc.) have less predictable parameters than the entering fluids. It is therefore advantageous to use analytic sensors on these fluids (as technology allows). Alternatively, fluids may be sampled for analysis. If cation or anion parameter sensors are not available, the system will display a range of historic values for the parameter in question to assist an attending physician, who may then select a value based both upon his or her professional judgment and upon the historical range values.

The invention provides a method of analyzing the content of a fluid, comprising the steps of using the measured volume of the collected fluids to convert said absolute concentration to the collecting the fluid for analysis; placing a first electrode in the fluid to be analyzed; positioning a second electrode in close proximity to the fluid to be analyzed; causing an electrical current to flow between the second electrode and the fluid so as to create a spark or arc between the second electrode and the fluid; collecting the light emitted by the spark or arc; determining the amount of light emitted at wavelengths of interest; analyzing the amount of light emitted to determine the relative concentration of a substance of interest; using one or more reference measurements that represent the total concentration of substances present to convert the relative concentration of a substance to an absolute concentration; and, using the measured volume of the collected fluids to convert said absolute concentration to the total amount of the substance present in the fluid.

Fluid inputs and outputs are two factors in maintaining proper fluid and electrolyte values in a patient. A third factor, accounting for which is a further object of the invention, is the baseline parameters of the individual patient. The total body fluid and electrolyte values vary widely among patients depending upon their age, sex, body fat percentage, and weight. However, within a particular group of patients of the same sex, ages, body fat percentages, and weights, the values are predictable. The system of the present invention will thus have a predictor for the total body water and electrolyte values based upon a patient's sex, age, body fat percentage, and weight. In turn the body fat percentage may be estimated by a patient's age, sex, height, and weight, all of which are easily ascertainable. Improved values for body fat percentage may be determined by sensors currently becoming available. Examples of these sensors are triceps skin-fold thickness or bio-impedance measurement devices.

The invention's usefulness extends through preoperative procedures, actual operations, the postoperative care phase, and general patient care.

DETAILED DESCRIPTION OF THE PREFERRED EMBODIMENT

Figure 2:
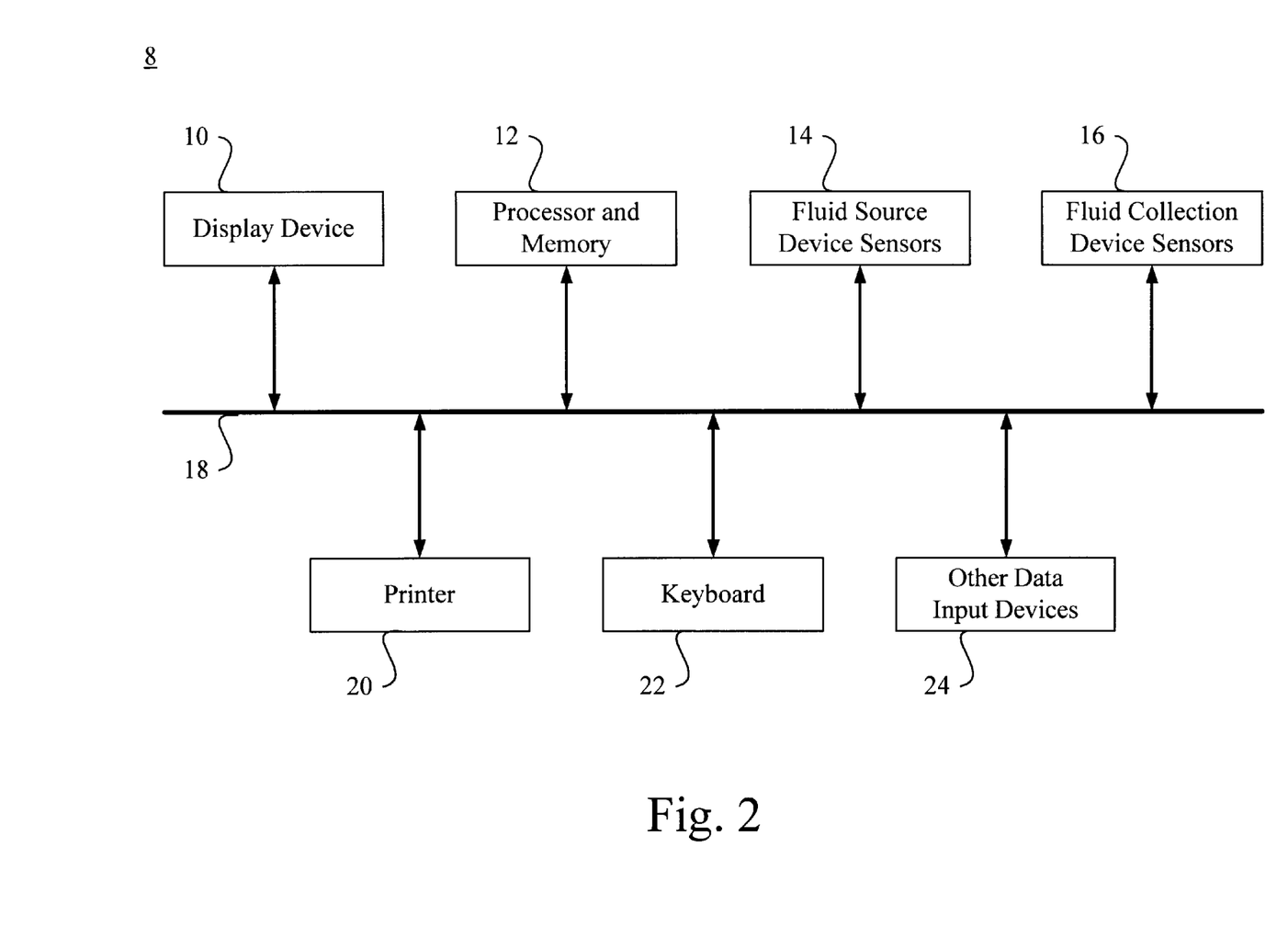
FIG. 2 is a block diagram illustrating components of a fluid and electrolyte balance monitoring system according to the invention.

Referring to FIG. 2 the invention includes a number of fluid source device sensors 14 and a number of fluid collection device sensors 16 each connected via a bus 18 to a digital processor and memory 12. An attending physician inputs additional data through a keyboard 22, and through optional other data input devices 24 such as bar code readers. The attending physician receives information through a display device 10 and through hardcopies printed on a printer 20. The actual configuration of the system and the details of the selection of appropriate sensor technologies depend in part on ongoing cost-benefit analysis as the sensor technologies and prices change over the production lifetime of the system.

Figure 3:
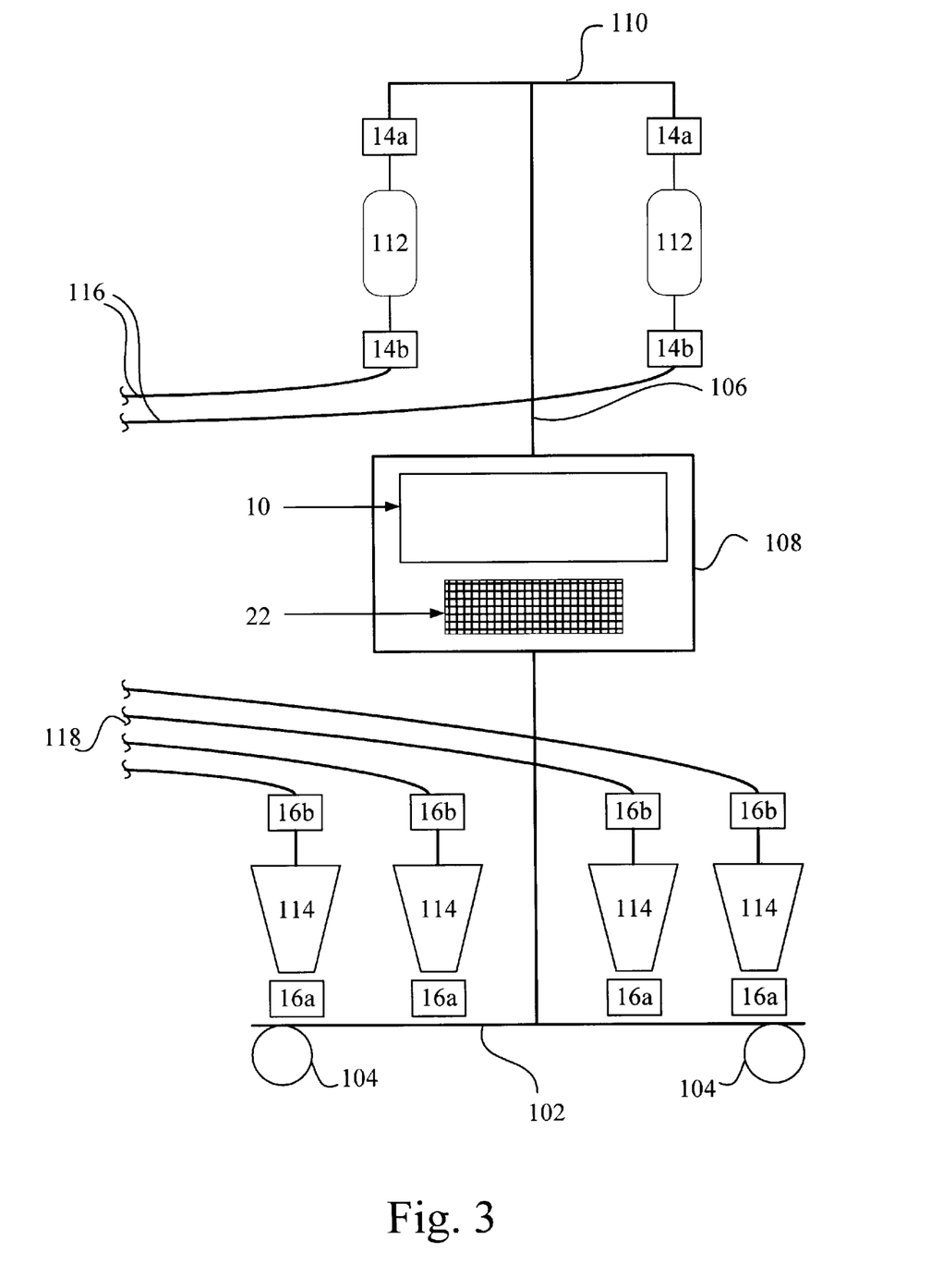
FIG. 3 shows the invention in an embodiment supported by a pole which facilitates gravity feed and system portability.

FIG. 3 shows several components of the invention in a preferred embodiment used with conventional fluid source devices 112 and fluid collection devices 114 all supported by an IV pole 100. IV pole 100 includes a base 102 mounted on casters 104 to facilitate movement. Mounted on base 102 is a vertical member 106 which supports a computer housing 108 at a height convenient for the attending physician. The housing 108 supports display device 10 and keyboard 22, and also encloses the system processor and memory 12 and provides connection points for optional data input devices 24 such as a bar code reader shown in FIG. 2.

Pole 100 further supports, via a cross member 110, the fluid source containers 112 and fluid source device sensors 14 at a height suitable for gravity feed of the fluids into a patient. Weight scales may be used to sense fluid volumes, although not to sense ion concentrations. If the fluid source device sensors 14 are weight scales, then the fluid source containers 112 rest on or hang from sensors 14a. Otherwise, fluid source device sensors 14b are attached to the output tubing 116 of the fluid source containers 112. The fluid collection containers 114 are supported preferably by the base 102 like the fluid source containers 112. If the fluid collection device sensors 16 are weight scales, then the fluid collection containers 114 rest on or hang from sensors 16a. Otherwise, fluid collection device sensors 16b are attached to input tubing 118 of the fluid collection containers 114.

The fluid source device sensors 14 measure the volume of fluid and the concentration of sodium or of potassium. When the electrolyte concentration is multiplied by the fluid volume, the result yields the total amount of an electrolyte species that is present in the fluid volume.

Several different mechanisms for measuring input fluid volumes are possible: a roller-pump 14b operating at a predetermined flow rate coupled with a timer in the digital computer 12; a scale 14a for continuously weighing the fluid and multiplying the weight by the specific gravity of the fluid to convert the weight to a volume; and in-line fluid flow sensors 14b. These technologies have differing advantages and disadvantages. Since the input fluids are going into a patient, sterility must be maintained. A roller-pump works by squeezing a plastic tube and, since it acts indirectly upon the fluid, sterility may be maintained by disposing of the plastic tubes after one use. However, there may be situations where the fluid should be administered to a patient by gravity feed rather than under pressure. In the case of weighing a fluid to derive its volume, again the determination of the fluid flow is by indirect means and sterility is maintained by using disposable bags and tubing. The use of weight scales also does not require that fluids be administered under pressure. Using in-line fluid flow sensors likewise does not require that fluids be administered under pressure, but has the drawback of requiring the sensors to be sterilized between uses or to be disposable. Roller-pump and in-line fluid flow sensors are typically more expensive and less accurate: therefore, the invention in the preferred embodiment uses weight scales.

Figure 4:
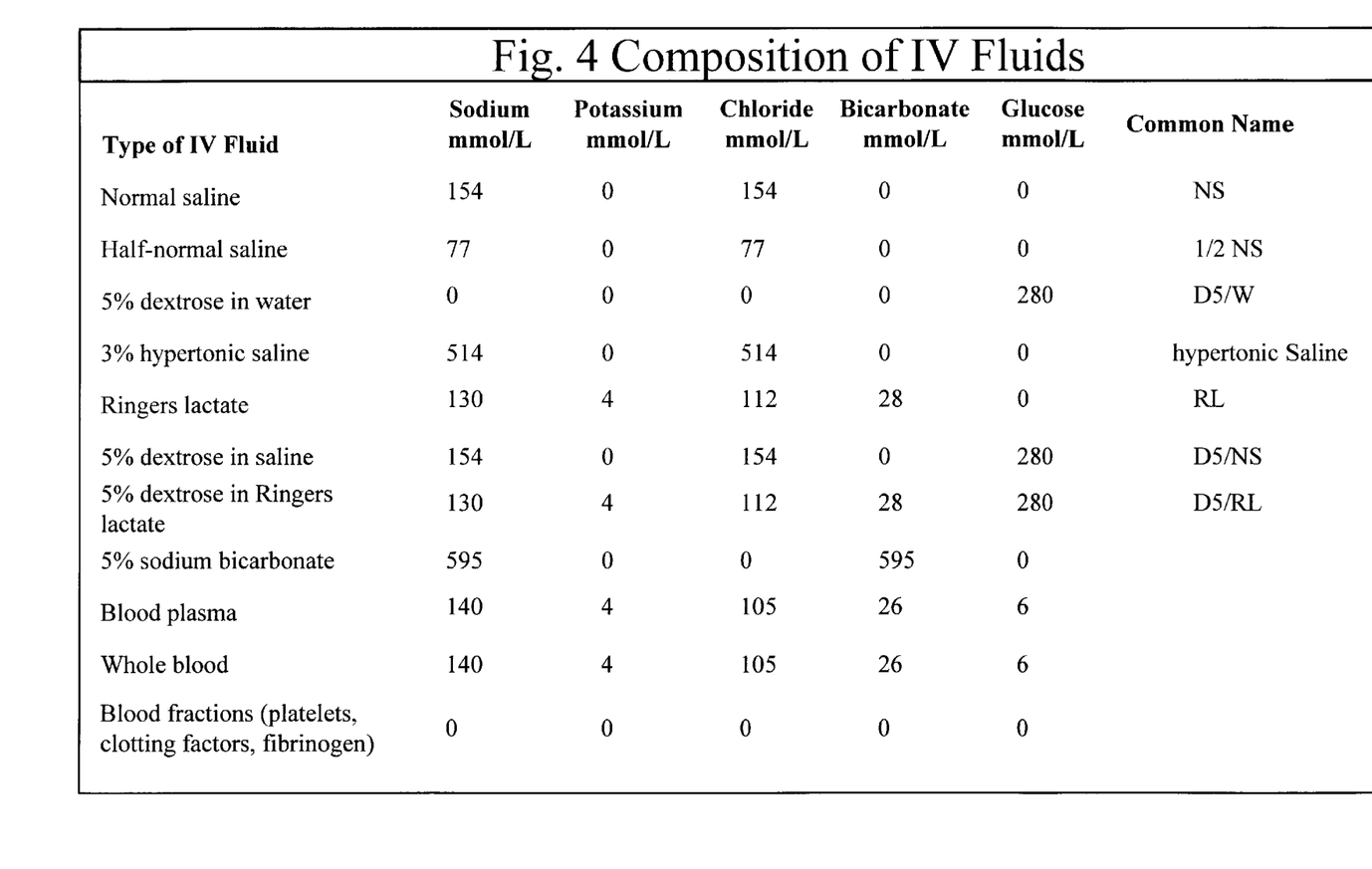
FIG. 4 is a table showing compositions of standard intravenous fluids.

The most commonly used postoperative fluids are described in FIG. 4. Determining the cation or anion concentrations of the various input fluids is simplified by the fact that the dozen or so typically administered fluids are manufactured or selected to have standard properties and to include standard amounts of the cations and anions essential to monitor: Sodium (Na+), Potassium (K+), and Chloride (Cl-). The cation or anion concentrations in the administered fluids may be determined in any of three different ways: 1) by the use of highly accurate analytic sensors; 2) by the use of confirmation sensors which only need a level of accuracy sufficient to confirm the parameters of the selected fluid; or 3) by attending physician entry in reliance on the labeling of the fluid bags. Loss of Magnesium (Mg++) from the body is also important to estimate but is generally not in any standard fluid that is administered.

Each of these methods has advantages and disadvantages. There are two times when errors can be made in the cation and anion concentration of a fluid: first when the fluid is prepared by the fluid manufacturer and put into a labeled bag, and second when an OR technician hangs the bag in preparation for its administration to a patient. The use of analytic sensors can detect both kinds of errors, but at a cost of complexity and the need for recurring calibration. Again, these sensors risk low reliability due to the need for sterility and autoclaving. The use of less costly confirmation sensors (osmolarity, chloride conductivity) only allows the detection of gross errors at the time of use of the fluid, and does not detect errors made during the manufacture of the fluid bag. However, it has been found that in the administration of fluids the overwhelming majority of errors, numerically still rare, arise from an OR technician hanging the wrong bag of fluid. The use of confirmation sensors adds a reasonable level of protection against this eventuality without unreasonably increasing the complexity and cost of an IV system. In any case, manual or manually assisted entry of data concerning input fluid factors is adequate. A physician directing the administration of a fluid can enter the short name of the fluid or press an appropriate function key at the system keyboard 22, and the digital computer 12 then looks-up cation or anion concentration values from a table. Alternately a physician can use a manually assisted data entry device such as a bar-code wand to enter cation or anion concentration values.

Monitoring the output fluids presents different problems than monitoring the input fluids. Since the fluids are leaving a patient, the sterility of system components is not an issue, but the requirements for sensors are greater due to the non-standard nature of the output fluids. The output fluids needing to be monitored include:

1) emesis (vomit)
2) gastric drainage
3) chest tube drainage
4) laparoscopy drainage
5) diarrhea
6) biliary drainage
7) urine
8) third space loss
9) blood A series of receiving containers 114 captures the volumes of these fluids. There are several technologies available for determining the volumes. A weight scale is a reasonable technology. The volumes of fluids in the receiving containers can also be measured by using sound or an interrupted light beam to determine the free air space left in a container 114. Alternatively, a single collection cannister can receive all output fluids so that only the total volume of all output fluids is measured, not the individual output fluid volumes.

There are several kinds of output fluids which will defy analytic measurement but cannot be ignored. The most important ones are the third space fluids and the blood residing in or on lap sponges and other surgical implements. An attending physician will need to estimate the third space losses and manually enter the values into the system. Lap sponges can be weighed and the dry weight of the sponges subtracted to find the weight of the blood alone, which can then be converted to volume by using the specific gravity of whole blood as a best estimate.

Figure 5:
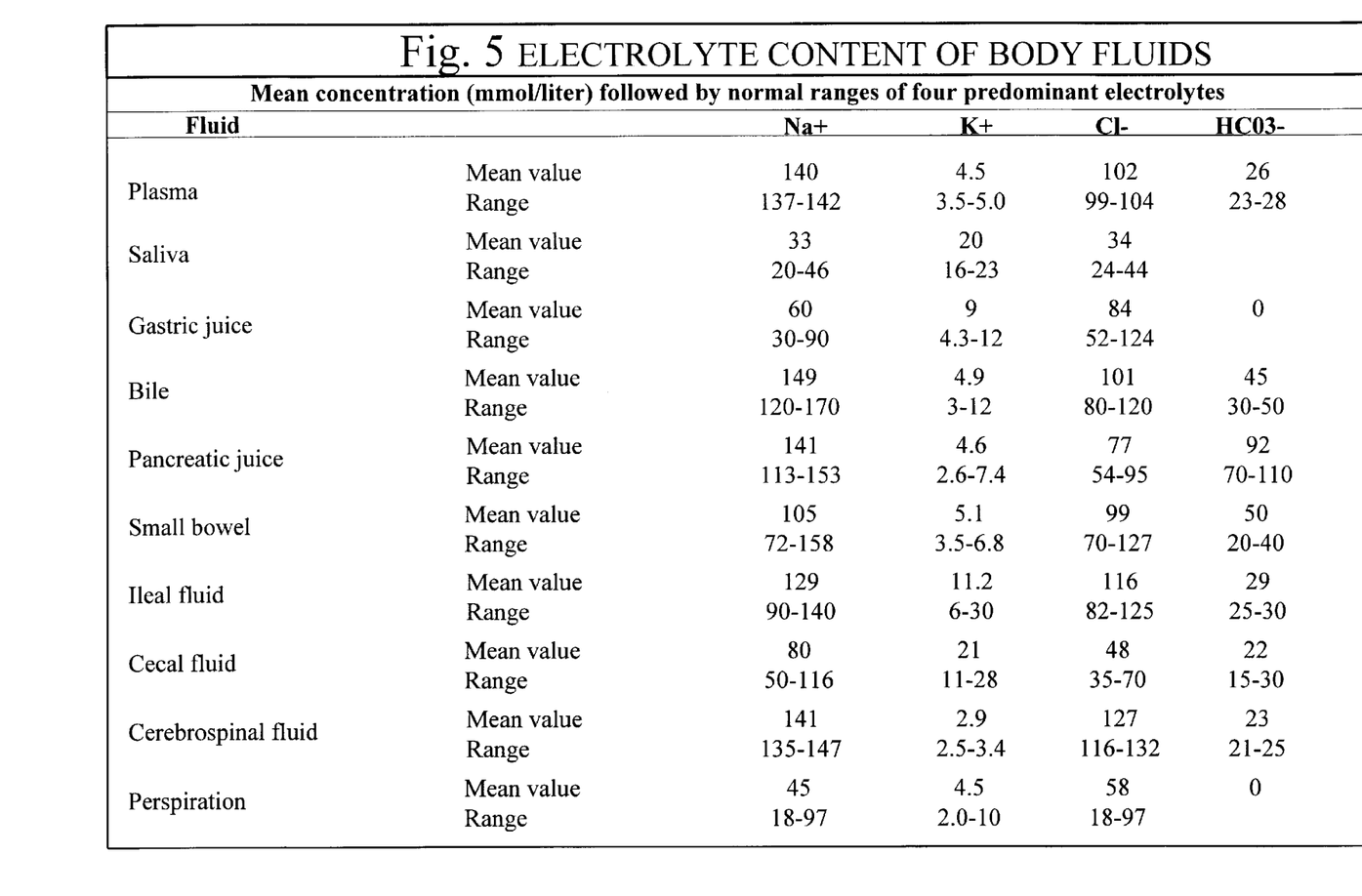
FIG. 5 is a table showing electrolyte content for some body fluids.

The concentrations of cations and anions in each of these fluids varies between patients. Averages and ranges for some of these are given in FIG. 5. The use of low accuracy "confirmation" sensors, which might be sufficient to identify the type of fluid being administered from the handful of known fluids used in IV therapy, would not be sufficient to identify the electrolyte concentrations in the fluids being collected, which would be much more variable. One method of measuring these concentrations applies techniques from analytical chemistry to accurately measure the amount of different electrolytes present. Currently available sensors which are suitable for use include ion specific electrodes, flame photometers, and sensors which directly measure electrical properties of a fluid. Using sensors could be the most accurate technique but there are practical problems of availability of reasonably priced sensors.

The present invention provides novel solutions to the problem of making quantitative measurements of the body fluids being analyzed. This invention provides an IOMeter™ with a new method of flame photometry that uses an electrical discharge, using either direct current or a radiofrequency current, to create a spark for measuring fluid properties. The spark ionizes a portion of the fluid being measured and the atomic composition of the fluid determines the optical properties of the light emitted by the spark.

A first embodiment, to ionize atoms present in the fluid to be analyzed, generates a spark in the air gap between a first electrode positioned in the fluid and a second electrode positioned out of the fluid. Alternatively, a spark may be created by placing a first electrode and a wick both in the fluid and placing a second electrode out of the fluid but in contact with the surface of the wick. This causes ions near the surface of the fluid to emit light unaffected by the optical properties of the fluid. It also allows an optical fiber to be positioned outside of the fluid where the fiber can remain clean and not become covered by fluid residue as would occur if it were positioned inside the fluid.

Figure 6:
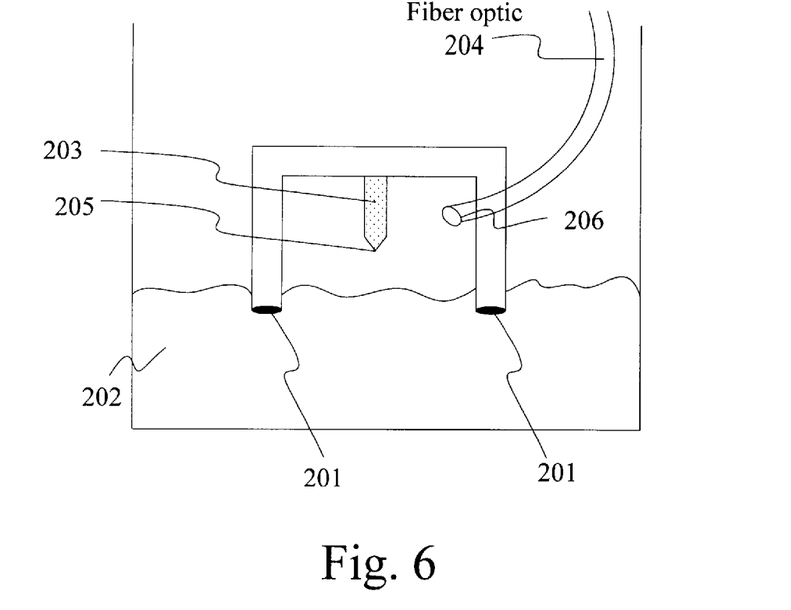
FIG. 6 is a schematic side view of a spark-photometer sensor for analyzing output fluids according to the invention.

As shown in FIG. 6, a first electrode 201 of sufficiently large surface area is positioned in contact with the fluid 202, for example around the circumference of a cylindrical tube floating on the surface of the fluid. A second electrode 203 of small surface area and optionally drawn to a point 205 is positioned in contact with, or in close proximity to, the surface of the fluid 202. An optical fiber 204 and optional coupling lens 206 is positioned out of the fluid and aimed to collect the light emitted when a spark jumps the gap from second electrode 203 to the fluid surface 202. The light is then sent to an optical spectral analysis unit which can be a fiber optic spectrometer or simply narrowband interference filters centered at the sodium and potassium spectral lines of interest, and optical detectors. The intensity of the light is analyzed by known means to yield information about the electrolyte concentration in the fluid. This information can not be considered quantitative until further information is obtained.

In biological fluids, the predominant positive ions are sodium and potassium. This means that a measurement of the electrical conductivity of the fluid can yield information about the total number of positive ions, or the total amount of sodium and potassium. Since the electrical conductivity of a fluid is strongly influenced by temperature, this must be measured or controlled. The measurement of electrical conductivity is a simple method for calibration without requiring the measurement of reference solutions or the addition of other elements in known quantities.

Figure 7:
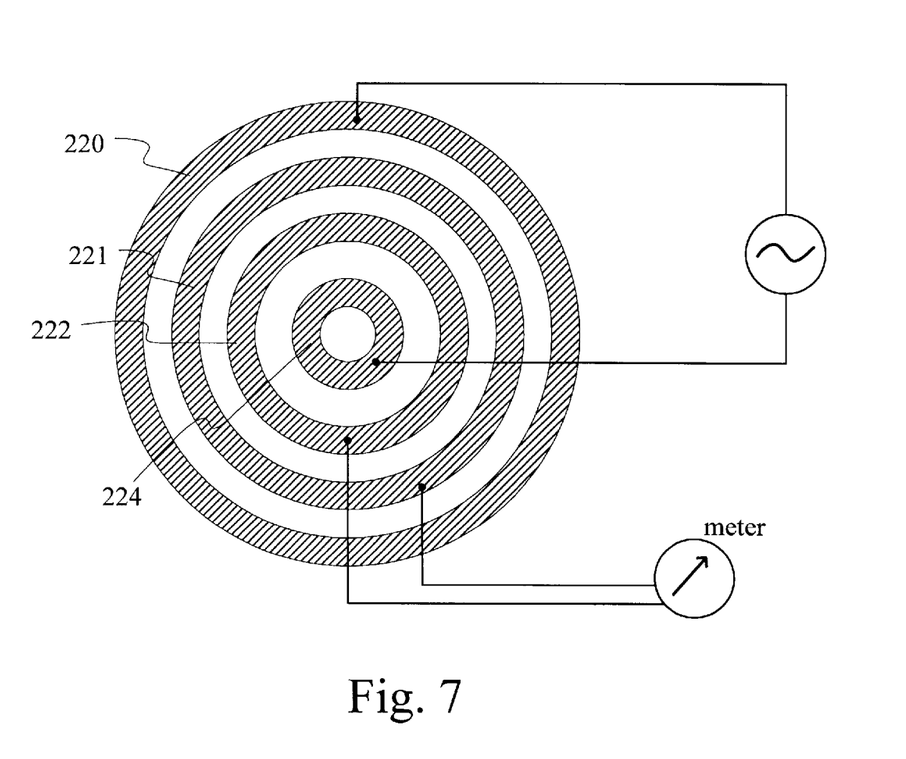
FIG. 7 is a bottom view of the sensor of FIG. 6 in an embodiment with multiple concentric electrodes.

Electrical conductivity is conventionally measured using four electrodes immersed in the fluid. Two electrodes are used to send an electric current through the fluid and the other two are used to sense the voltage developed. The electrode 201 of FIG. 6 can serve dual purposes in this sensor. If it is made of four concentric rings, all four rings can be connected together via switches to form the return electrode for the spark generator. When not producing a spark, they can be disconnected from the spark generator and connected as described above for measuring electrical conductivity. FIG. 2 shows a bottom view of the sensor of FIG. 6. There are four concentric rings 220, 221, 222, 223 and a temperature sensor 224. Thus the FIG. 6 sensor can measure the electrical conductivity of the fluid, the temperature of the fluid, and optical emission from a spark. The electrical conductivity of the fluid and temperature yields information about the total concentration of sodium and potassium, the analysis of optical emission from the spark gives information about the relative concentrations of sodium and potassium compared to each other, and these two pieces of information, through simple algebra, give the concentrations of sodium and potassium.

If a reference solution is desirable or required to obtain the desired degree of accuracy, one can be used and made to serve multiple purposes. In addition to providing a standard of known concentrations of sodium and potassium or some other reference element not found in body fluids in any significant amount, such as lithium, it can also have other properties. It can contain a disinfectant to make the body fluid discharges safer for nursing personnel to handle. It can contain an odor control formulation to reduce unpleasant odors. It can also contain substances like surfactants to enzymatically break down the body fluids and make them less likely to stick to the spark electrodes.

Figure 8:
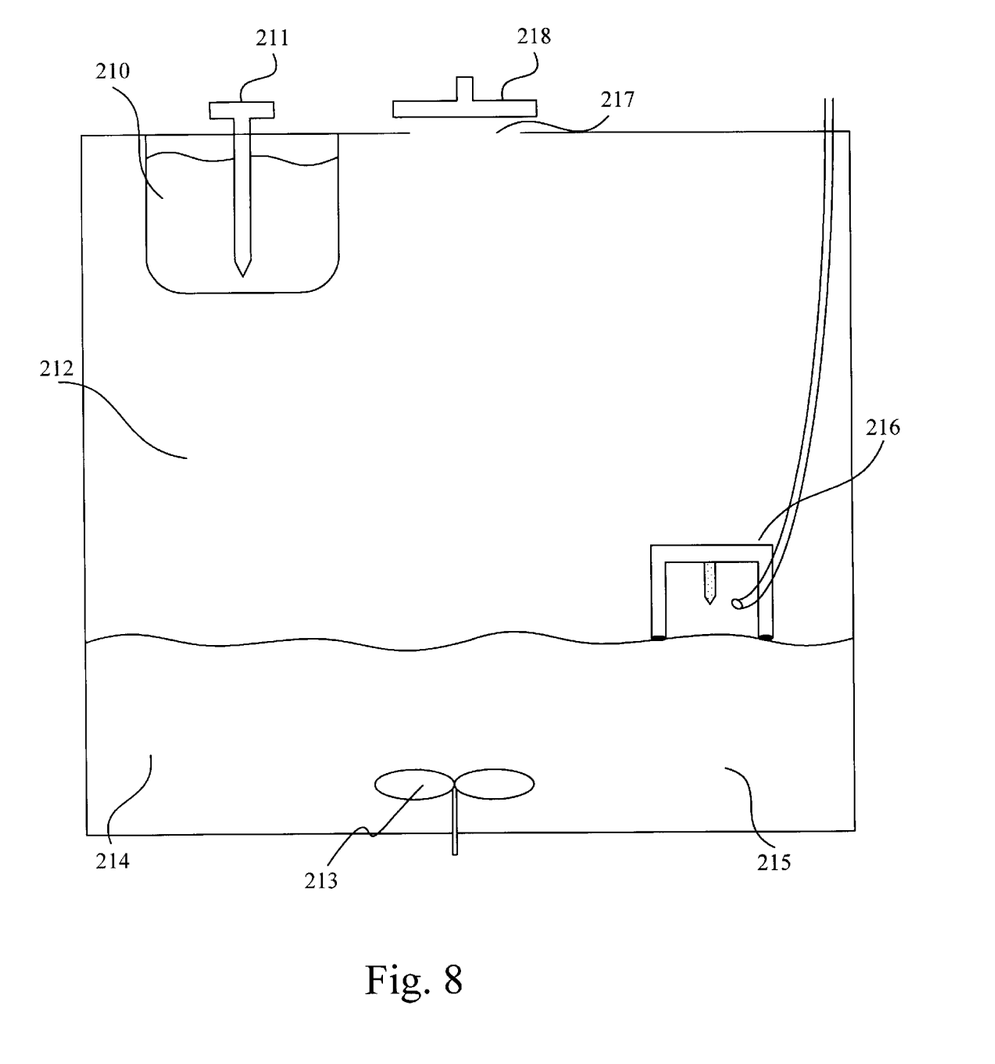
FIG. 8 is a side cut-away view of a collection canister.

FIG. 8 shows an example of a collection canister 212 suitable for a single use over a 24 hour time period. Prior to use, a reference fluid is contained in a reservoir 210 that can be punctured by a dispensing means 211 to deliver a known volume of a reference solution with a known composition to the collection canister 212. A stirring element 213 located in the bottom of canister 212 circulates the collected fluid 214 to ensure that it is completely mixed. A filter membrane 215 separates a section of the canister where the electrical conductance/spark photometer sensor 216 is located. This prevents large debris from entering the region where the measurements will be made and potentially clogging up the sensor.

In use, the canister, containing a known amount of the reference fluid, but no collected fluid, is positioned in the IOMeter™ and weighed to "tare" the scale that calculates volume from weight. Next, dispensing means 211 is activated to break through the bottom surface of the reference fluid reservoir which then empties into the collection canister below. Sensor 216 then makes a reference measurement of the electrical conductivity of the fluid and the optical intensities at all wavelengths of light of interest that are emitted from a spark discharge inside the sensor. The system is then ready to begin operation.

As body fluids are collected by the canister through opening 217, closed by lid 218 when fluids are not being collected, the total fluid volume in the canister increases and the concentrations of sodium, potassium, and the reference element change. The concentrations of sodium and potassium can either increase or decrease depending on the composition of the fluid being collected, but the concentration of the reference fluid can only decrease since it is assumed that it is not present in the body fluids being collected. Thus, the tared weight of the canister will change, the electrical conductivity of the fluid in the canister will change, and the optical intensities at all wavelengths of light of interest that are emitted from a spark discharge inside the sensor will also change. This information is used to compute the total sodium and potassium in mmol that has been discharged from the patient.

Figure 9:
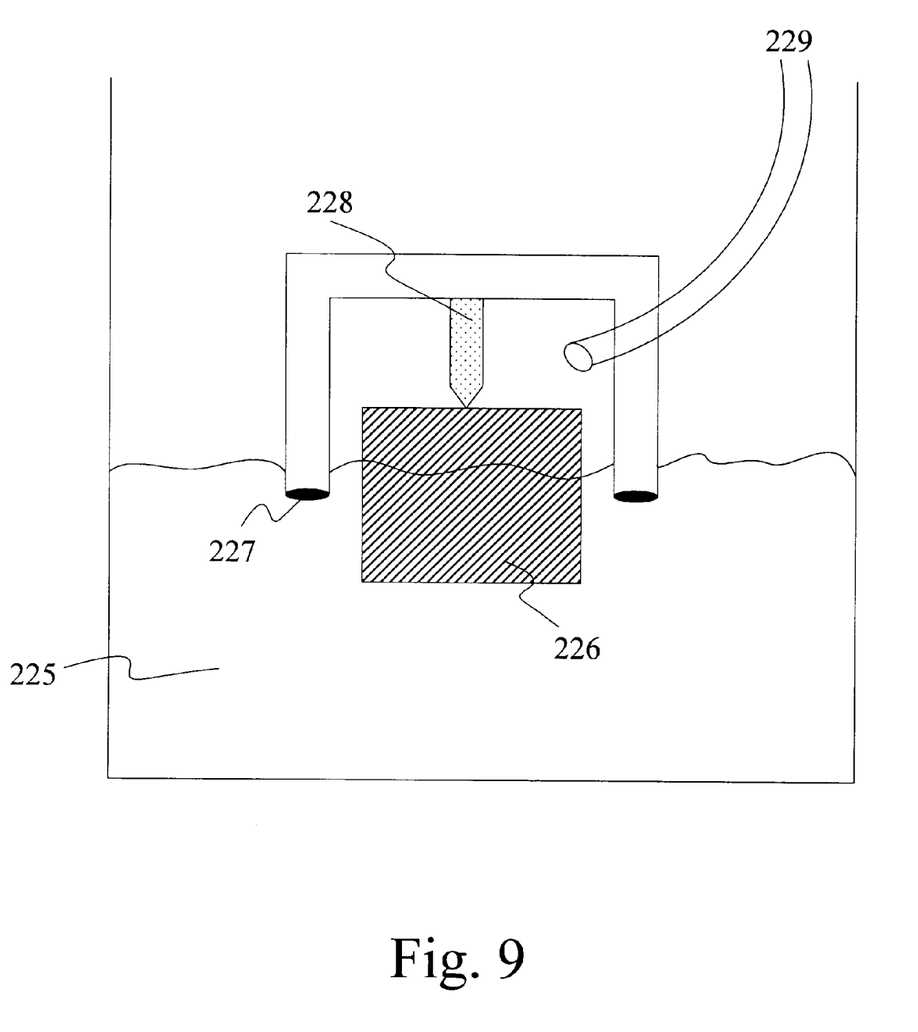
FIG. 9 is a schematic side view of a second embodiment of a spark-photometer sensor according to the invention.

FIG. 9 is a schematic cross-section of a sensor in an embodiment having a wick 226 in contact with, and therefore wet by, the fluid 225. First electrode 227 is in fluid 225 or may be in contact with the wet part of wick 226. Second electrode 228 touches, or is in close proximity to, and allows a spark or arc to, the surface of wick 226. Light emitted by the spark or arc is transmitted through fiber optic 229 to be analyzed as explained with reference to FIG. 6.

Figure 10:
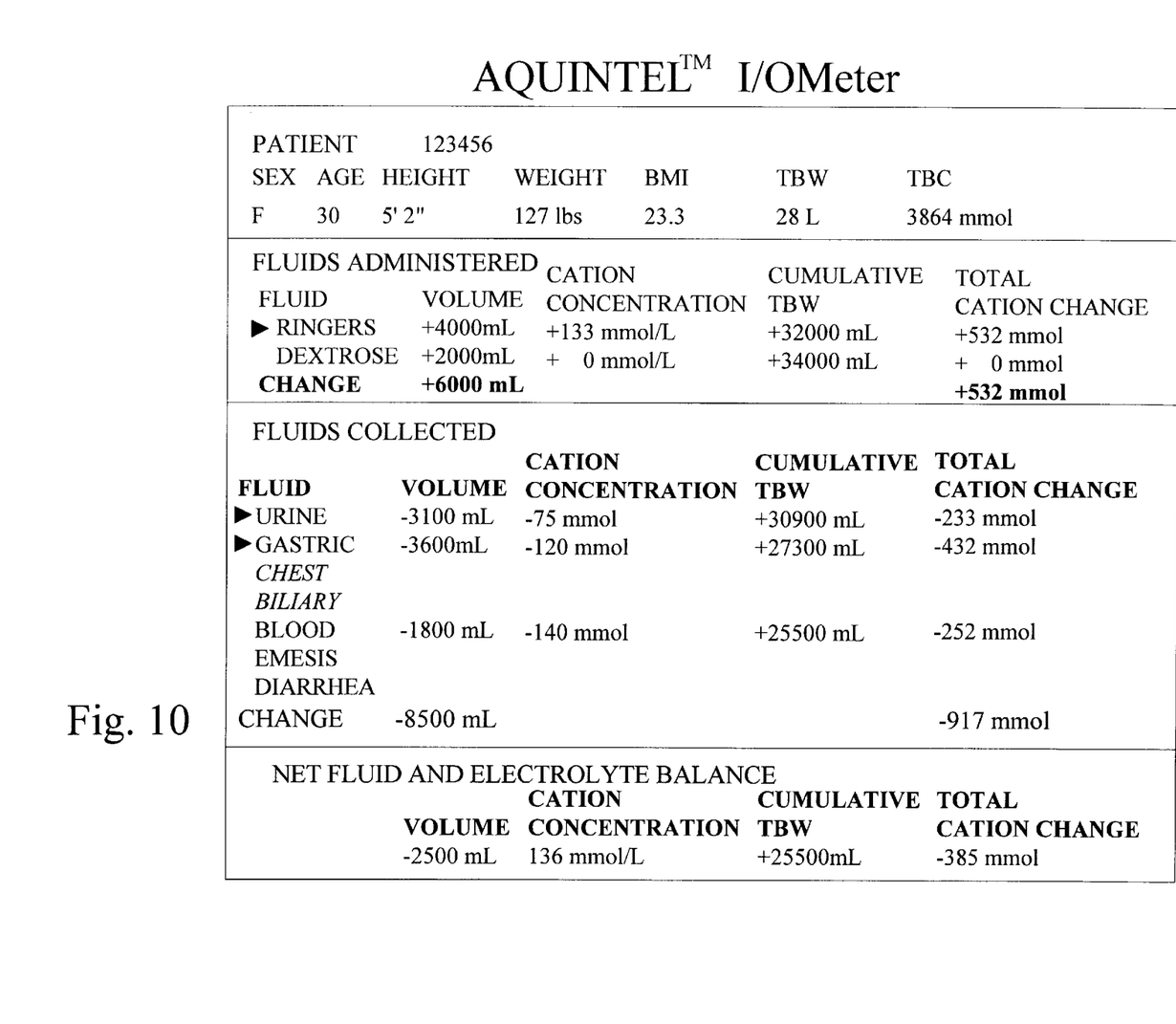
FIG. 10 shows a representative front panel display for use by an attending physician.

The invention has a display device 10 as shown schematically in FIG. 2 which gives to an attending physician a readout as shown in a typical view in FIG. 10. The display device 10 can be either a Cathode Ray Tube (CRT) display, a gaseous plasma display, or a Liquid Crystal Display (LCD). The preferred embodiment uses an LCD display, as these devices' thinness allows mounting them on the housing 108 immediately above keyboard 22. When patient care is initiated, an attending physician scrolls through the entry fields displayed on display device 10 and enters values from a patient's medical records. Other fields are controlled by digital processor 12, either through interpreting sensor data or through the intervention of an attending physician. Such intervention may be because of a direction to administer a given fluid (e.g. give 1 liter of NS) or when the physician must manually enter estimated fluid parameters for those outgoing fluids which cannot be analyzed automatically. In the later case the physician will enter the generic outgoing fluid type (e.g. urine) and receive displayed historic values for the average and standard deviation of that fluid's cation and anion concentration. The physician will then select the value that he or she believes to be the best approximation for a particular patient.

The preferred embodiment has a keyboard for the attending physician to enter data. Since there are only a dozen input fluids in wide use and only about 10 outgoing fluids which require tracking, individual function keys preferably are assigned to each type of fluid. Additional alphanumeric keys allow entering unusual fluid types and the numeric input of data as described above.

A digital processor and memory are shown in the system block diagram of FIG. 2. The digital processor and memory will be located in the system housing which houses the display device and keyboard. Because the processing capacity requirements are relatively slight, this may be a low powered microprocessor or microcontroller.

The preferred embodiment also includes a printer 20 or other hardcopy device attached to the system bus 18 as shown in FIG. 2. The output device can be mounted almost anywhere within a reasonable distance from computer housing 108, but is preferably mounted on the side of the housing 108 opposite the display device 10 and keyboard 22. For clinical use, histories will be printed on standard (8.5 by 11 inch) sized sheets of paper.

Up until this point, measurements of the volumes and cation or anion concentrations of the input and output fluids have been discussed. It is also necessary to produce a baseline for the fluids in a patient. The system uses look-up tables to estimate a patient's total body water (TBW) and electrolyte content. The system display 10 displays prompts to an attending physician, who then enters values for a patient's age, sex, height, and weight. The system then calculates a derived value for percentage body fat (body mass index (BMI)) using the formula BMI=(patient's weight in Kg/(patient's height in cm)$^2$) and uses this value in conjunction with the other entries to derive the patient's total body water and electrolyte content. The following simplified list illustrates such a look-up table:

| Age | Male | Female |
|---|---|---|
| 10–18 | 59 | 57 |
| 18–40 | 61 | 51 |
| 40–60 | 55 | 47 |
| over 60 | 52 | 46 |
| obese & over 60 | 45 | 40 |

More accurate values for percentages of body fat may be obtained by various tests, instruments, and sensors. It is likely that the commercially produced version of the invention will utilize one of these measured values. One such instrument is the triceps pinch, which pinches a skin fold on a patient's upper arm and gives an improved value for percentage body fat compared to the body mass index as calculated above. A laboratory test for tritium content in a patient's blood also yields an improved value for percentage body fat. A recently developed special scale upon which a patient stands barefoot uses bioimpedance measurements to give a direct digital value for percentage body fat. However, even when the above measurements cannot be made (e.g. a patient has burns preventing use of the triceps pinch), estimates based upon age, sex, height, and weight are always available.

Figure 11:
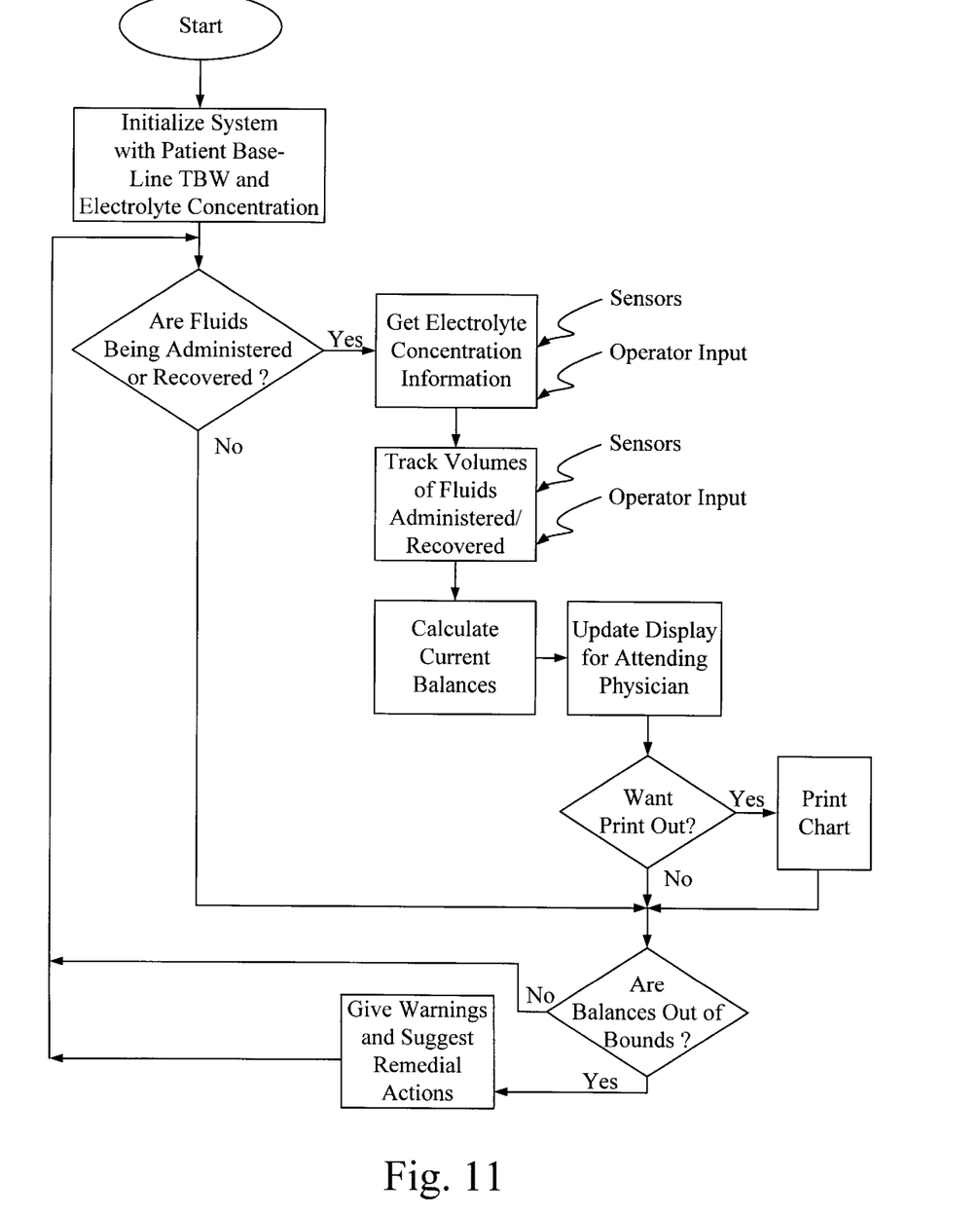
FIG. 11 shows a representative process flowchart describing the monitoring functions of the invention.

As shown in the flowchart of FIG. 11, once the system contains baseline information about the patient's TBW and cation or anion concentration, the system enters its monitoring mode. The software continuously monitors the input and output fluids from the patient for volume and cation or anion concentration. In some cases the monitoring will be fully automatic while in other cases an attending physician will intervene. In the preferred embodiment of the invention, when it is necessary to administer fluids to a patient the attending physician directs the OR technician to hang the appropriate plastic bag 112 of fluid from the cross member 110 and then connect this via IV tubes 116 to the patient. Depending upon the precise implementation of the invention, the attending physician enters information about the fluid bag 112 manually via the keyboard 22 or semi-automatically via a bar code reader 24. The system software first checks the entered values of the cation or anion concentrations by comparing them with the signals from the ion concentration sensor (if available), and then continuously monitors the amount of fluid given using the weight scale or fluid flow sensor 14. This allows for near-real-time calculations of the patient's current fluid and electrolyte balance values. These values are compared with boundary values beyond which the patient may exhibit pathology.

Fluids leaving the patient are tracked in a similar manner. As an example, a urinary catheter is attached via tubing to a fluid output container 114 at the base 102 of the invention. The attending physician indicates that fluid to be monitored is urine, and the system displays the mean and standard deviation of cation and anion concentrations in urine. The attending physician then enters cation and anion concentration values corresponding to the patient's condition (e.g. the urine from a dehydrated patient has above-normal concentrations of Na+). The system will again continuously monitor the volume of the fluid and again update in near-real-time the patient's fluid and electrolyte balance values.

If the system ever detects a value of the patient's fluid and electrolyte balances which is out of permissible bounds, it uses visual (flashing lights) and audible (tone) signals to attract the attention of the attending physician. The display will show exactly what the problem is and suggest corrective fluid application.

Hypothetical Patient:

A 30-year-old woman patient weighs 127 lbs. (58 kg). From the literature, her total body water (TBW) is found to be 28 liters. Prior to an operation, her plasma Na is 138 mmol/L, K is 4.0 mmol/L, and hematocrit is 40%.

The patient then has a gastric resection surgery for ulcer disease, during which she receives 4 liters (4000 ml) of Ringers lactate and loses an estimated 1800 ml. of blood.

During the initial 24 hours post-operatively she is given 2000 ml of 280 mmol/L glucose in water (5% dextrose in water) intravenously, which has no electrolyte. Post-operatively, she loses 3.6 liters of gastric suction and 3.1 liters of urine. After the initial 24 hours, her plasma Na is 136 mmol/L and K is 3.6 mmol/L.

Figure 12:
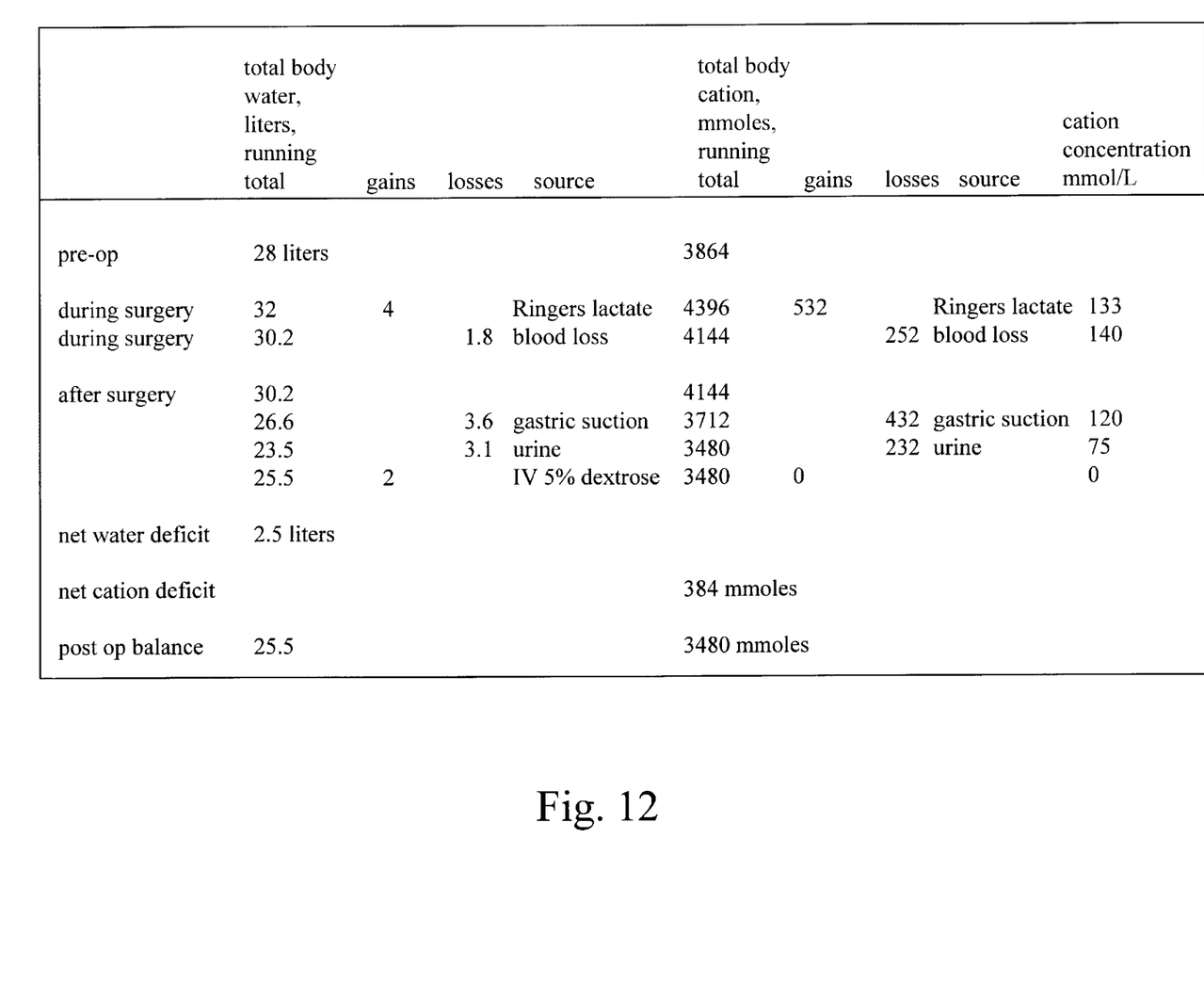
FIG. 12 shows running totals of Total Body Water and total body cation for an example patient through the course of an operation and post-op period.

What is the patient's fluid status at the end of the initial 24 hours; and what should be done? The balance data is summarized in FIG. 12.

Prior to surgery, her balance was:
28 liters of total body water (48% of body weight)
Total body cation (Na+K)=28 L×138 mmol/L=3864 mmoles
Immediately after surgery, her balance was
30.2 liters water and 4144 mmoles cation Thus, after the initial 24 hours, the net fluid and electrolyte balance shows a deficit of 2.5 liters water and a deficit of 384 mmoles cation. This can be repaired with 2.5 liters intravenously of isotonic saline (154 mM NaCl).

The exemplary embodiments described herein are for purposes of illustration and are not intended to be limiting. Therefore, those skilled in the art will recognize that other embodiments could be practiced without departing from the scope and spirit of the claims set forth below.

What is claimed is:

1. A fluid and electrolyte balance monitoring system, comprising:

input fluid measuring means for measuring a volume of input fluid that will enter a patient;

input fluid analyzing means for determining electrolyte parameters of said input fluid;

output fluid measuring means for measuring a volume of output fluid that has exited the patient;

flame photometry means for determining electrolyte parameters of said output fluid; and fluid volume and electrolyte tracking means for calculating and monitoring a fluid volume status and an electrolyte status of the patient based on information obtained from said input fluid measuring means, said input fluid analyzing means, said output fluid measuring means, and said flame photometry means.

2. A method for monitoring fluid and electrolyte balances, comprising the steps of:

measuring a volume of input fluid that will enter a patient;

determining electrolyte parameters of the input fluid;

measuring a volume of output fluid that has exited the patient;

determining electrolyte parameters of the output fluid using flame photometry; and calculating and monitoring a fluid volume status and an electrolyte status of the patient based on the measured volume of the input fluid, the determined electrolyte parameters of the input fluid, the measured volume of the output fluid, and the determined electrolyte parameters of the output fluid.

3. The method of claim 2, wherein determining output fluid electrolyte parameters comprises the steps of:

positioning a first electrode in the output fluid;

positioning a second electrode in close proximity to the output fluid;

causing an electrical current to flow between the second electrode and the output fluid so as to create a spark or arc between the second electrode and the output fluid;

collecting the light emitted by the spark or arc;

determining the amount of light emitted at wavelengths of interest;

analyzing the amount of light emitted at wavelengths of interest to determine concentrations of substances of interest; and using the output fluid volume to convert the concentrations to total amounts of the substances of interest present in the fluid.

4. The method of claim 3, wherein a reference fluid containing known concentrations of certain substances is first analyzed to establish a reference for the amount of light emitted at wavelengths of interest.

5. The method of claim 4, wherein the reference fluid contains known concentrations of one or more substances expected to be found in the output fluid.

6. The method of claim 4, wherein the reference fluid contains known concentrations of one or more substances not expected to be found in the output fluid.

7. The method of claim 2, wherein determining output fluid electrolyte parameters comprises the steps of:

positioning a first electrode in the output fluid;

positioning a second electrode in close proximity to the output fluid;

causing an electrical current to flow between the second electrode and the output fluid so as to create a spark or arc between the second electrode and the output fluid;

collecting the light emitted by the spark or arc;

determining the amount of light emitted at wavelengths of interest;

analyzing the amount of light emitted at wavelengths of interest to determine a relative concentration of a substance of interest;

using one or more reference measurements that represent the total concentrations of substances present to convert the relative concentration of the substance of interest to an absolute concentration; and using the output fluid volume to convert the absolute concentration to a total amount of the substance of interest present in the fluid.

8. The method of claim 7 wherein the electrical conductivity of the output fluid is measured at one or more alternating current frequencies and the electrical conductivity measurements are used as the reference measurements to convert a relative substance concentration to an absolute substance concentration.

* * * * *